(12) United States Patent
Bergmann et al.

(10) Patent No.: US 12,415,831 B2
(45) Date of Patent: Sep. 16, 2025

(54) HPLC FREE PURIFICATION OF PEPTIDES BY THE USE OF NEW CAPPING AND CAPTURE REAGENTS

(71) Applicant: Roche Diagnostics Operations, Inc., Indianapolis, IN (US)

(72) Inventors: Frank Bergmann, Penzberg (DE); Sebastian Johannes Pomplun, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 870 days.

(21) Appl. No.: 17/419,073

(22) PCT Filed: Jan. 3, 2020

(86) PCT No.: PCT/EP2020/050080
§ 371 (c)(1),
(2) Date: Jun. 28, 2021

(87) PCT Pub. No.: WO2020/144111
PCT Pub. Date: Jul. 16, 2020

(65) Prior Publication Data
US 2022/0064212 A1 Mar. 3, 2022

(30) Foreign Application Priority Data
Jan. 7, 2019 (EP) .................................... 19150578

(51) Int. Cl.
*C07K 1/20* (2006.01)
(52) U.S. Cl.
CPC ...................................... *C07K 1/20* (2013.01)
(58) Field of Classification Search
CPC ............. C07K 1/20; C07K 1/063; C07K 1/04
See application file for complete search history.

(56) References Cited

FOREIGN PATENT DOCUMENTS

| WO | 03017930 A2 | 3/2003 |
| WO | 2010032437 A1 | 3/2010 |

OTHER PUBLICATIONS

Canne, Lynne E. et al., Synthesis of a Versatile Purification Handle for Use with Boc Chemistry Solid Phase Peptide Synthesis, Tetrahedron Letters, 1997, pp. 3361-3364, vol. 38, No. 19.
Hara, Toshiaki et al., Peptide purification by affinity chromatography based on α-ketoacyl group chemistry, Journal of Peptide Science, 2009, pp. 369-376, vol. 15, No. 5.
Hara, Toshiaki et al., Peptide purification by affinity chromatography based on α-ketoacyl group chemistry, Journal of Peptide Science, 2009, pp. 369-376, vol. 15.
Hara, Toshiaki et al., Peptide purification using the chemoselective reaction between N-(methoxy)glycine and sothiocyanato-functionalized resin, Journal of Peptide Science, 2016, pp. 379-382, vol. 22, No. 6.
International Search Report issued Mar. 16, 2020, in Application No. PCT/EP2020/050080, 1 p.
Loibl, S. F. et al., Total chemical synthesis of proteins without HPLC purification, Chemical Science, 2016, pp. 6753-6759, vol. 7, No. 11.
Merrifield, R. B., Solid Phase Peptide Synthesis. I. The Synthesis of a Tetrapeptide, Journal of the American Chemical Society, 1963, pp. 2149-2154, vol. 85, No. 14.
Montanari, Vittorio and Kumar, Krishna, A Fluorous Capping Strategy for Fmoc-Based Automated and Manual Solid-Phase Peptide Synthesis, European Journal of Organic Chemistry, 2006, pp. 874-877, vol. 4.
Montanari, Vittorio and Kumar, Krishna, Just Add Water: A New Fluorous Capping Reagent for Facile Purification of Peptides Synthesized on the Solid Phase, Journal of the American Chemical Society, 2004, pp. 9528-9529, vol. 126, No. 31.
Shogren-Knaak, Michael A. et al., α-Chloroacetyl capping of peptides: an N-terminal capping strategy suitable for Edman sequencing, Tetrahedron Letters, 2000, pp. 827-829, vol. 41, No. 6.
Tartaggia, Stefano et al., Chemoenzymatic Synthesis of δ-Keto β-Hydroxy Esters as Useful Intermediates for Preparing Statins, European Journal of Organic Chemistry, 2016, pp. 3162-3165, vol. 19.
Villain, Matteo et al., Covalent capture: a new tool for the purification of synthetic and recombinant polypeptides, Chemistry & Biology, 2001, pp. 673-679, vol. 8, No. 7.
ISA/EP, Written Opinion issued in corresponding Application No. PCT/EP2020/050080, dated Mar. 16, 2020, 4 pp.
International Bureau of WIPO, International Preliminary Report on Patentability issed in corresponding Application No. PCT/EP2020/050080, dated Jul. 22, 2021, 6 pp.
"Peptide Synthesis," Sigma-Aldrich, ChemFiles, 2007, vol. 7, No. 2, 20 pp.

*Primary Examiner* — Sudhakar Katakam
(74) *Attorney, Agent, or Firm* — Taft Stettinius & Hollister LLP (57) ABSTRACT

The present disclosure relates to the use of a capping and capture reagent in solid phase peptide synthesis. The present disclosure further relates to a method of solid phase peptide synthesis, wherein a capping and capture reagent according to the present disclosure is used. The present disclosure further relates to a method for purification of a (full-length) synthetic peptide via use of a capping and capture reagent according to the present disclosure. The present disclosure also relates to a kit comprising a capping and capture reagent according to the present disclosure and an amino oxy resin or a hydrazine resin and the use of the kit.

4 Claims, 7 Drawing Sheets
Specification includes a Sequence Listing.

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: test agent

<400> SEQUENCE: 1

Trp Glu Gly Ser Lys Tyr Ala
1               5

<210> SEQ ID NO 2
<211> LENGTH: 5
<212> TYPE: PRT
<213> ORGANISM: Artificial Sequence
<220> FEATURE:
<223> OTHER INFORMATION: test agent
<220> FEATURE:
<221> NAME/KEY: MISC_FEATURE
<222> LOCATION: (1)..(1)
```

```
<223> OTHER INFORMATION: keto-capped

<400> SEQUENCE: 2

Gly Ser Lys Tyr Ala
1               5

<210> SEQ ID NO 3
<211> LENGTH: 10
<212> TYPE: PRT
<213> ORGANISM: Homo sapiens

<400> SEQUENCE: 3

Asp Arg Val Tyr Ile His Pro Phe His Leu
1               5                   10

<210> SEQ ID NO 4
<211> LENGTH: 4
<212> TYPE: PRT
<213> ORGANISM: Artificial Sequence
<220> FEATURE:
<223> OTHER INFORMATION: test agent
<220> FEATURE:
<221> NAME/KEY: MISC_FEATURE
<222> LOCATION: (1)..(1)
<223> OTHER INFORMATION: keto-capped

<400> SEQUENCE: 4

Pro Phe His Leu
1

<210> SEQ ID NO 5
<211> LENGTH: 28
<212> TYPE: PRT
<213> ORGANISM: Homo sapiens

<400> SEQUENCE: 5

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 5
<212> TYPE: PRT
<213> ORGANISM: Artificial Sequence
<220> FEATURE:
<223> OTHER INFORMATION: test agent resin-bound
<220> FEATURE:
<221> NAME/KEY: MOD_RES
<222> LOCATION: (5)..(5)
<223> OTHER INFORMATION: resin-bound

<400> SEQUENCE: 6

Ser Lys Ser Tyr Ser
1               5

<210> SEQ ID NO 7
<211> LENGTH: 5
<212> TYPE: PRT
<213> ORGANISM: Artificial Sequence
<220> FEATURE:
<223> OTHER INFORMATION: test agent resin-bound
<220> FEATURE:
```

```
<221> NAME/KEY: MISC_FEATURE
<222> LOCATION: (5)..(5)
<223> OTHER INFORMATION: resin-bound

<400> SEQUENCE: 7

Gly Ser Lys Tyr Ala
1               5
```

HPLC FREE PURIFICATION OF PEPTIDES BY THE USE OF NEW CAPPING AND CAPTURE REAGENTS

This application is a U.S. National Phase Application of International Application No. PCT/EP2020/050080 filed Jan. 3, 2020, claiming priority to European Application No. 19150578.3 filed Jan. 7, 2019, the disclosures of which are hereby incorporated by reference in their entirety.

The present invention relates to the use of a capping and capture reagent in solid phase peptide synthesis. The present invention further relates to a method of solid phase peptide synthesis, wherein a capping and capture reagent according to the present invention is used. The present invention further relates to a method for solid phase peptide synthesis wherein during peptide synthesis a capping and capture reagent according to the present invention is used facilitating afterwards the purification of (full-length) synthetic peptide. The present invention also relates to a kit comprising a capping and capture reagent according to the present invention and an amino oxy resin or a hydrazine resin and the use of said kit.

Solid-phase peptide synthesis (SPPS) is the mainstay method for the synthesis of small- to medium-length peptides (Merrifield, R. B., Solid Phase Peptide Synthesis. I. The Synthesis of a Tetrapeptide. *Journal of the American Chemical Society* 1963, 85 (14), 2149-2154). Especially the Fmoc-based strategy has prevailed as the mainly used methodology (W. C. Chan P. D. White Eds., *Fmoc Solid Phase Peptide Synthesis, A Practical Approach*. Oxford University Press: 2000). Despite the usually high coupling efficiencies a small amount of unreacted amino groups accumulate during the stepwise synthesis. To avoid the uncontrolled accumulation of deletion sequences missing one or more residues in different positions, after each coupling step a large excess of a capping reagent is added to the resin to ensure the complete deactivation of all remaining free amines. Usually acetic anhydride is used for this purpose. The most tedious and time-consuming aspect of SPPS remains the purification of the crude peptides by preparative HPLC. Despite the capping strategy some truncated sequences may co-elute with the full-length product and may be difficult to separate. To facilitate the purification issue various reagents have been developed for either tagging the incomplete sequences in order to modify their HPLC elution profiles or their solubility (Shogren-Knaak, M. A.; McDonnell, K. A.; Imperiali, B., α-Chloroacetyl capping of peptides: an N-terminal capping strategy suitable for Edman sequencing. *Tetrahedron Letters* 2000, 41 (6), 827-829; Canne, L. E.; Winston, R. L.; Ken, S. B. H., Synthesis of a versatile purification handle for use with Boc chemistry solid phase peptide synthesis. *Tetrahedron Letters* 1997, 38 (19), 3361-3364; Montanari, V.; Kumar, K., Just Add Water: A New Fluorous Capping Reagent for Facile Purification of Peptides Synthesized on the Solid Phase. *Journal of the American Chemical Society* 2004, 126 (31), 9528-9529; Montanari, V.; Kumar, K., A Fluorous Capping Strategy for Fmoc-Based Automated and Manual Solid-Phase Peptide Synthesis. *European Journal of Organic Chemistry* 2006, 2006 (4), 874-877). Alternatively, the full-length peptides have been modified in the last step with a moiety, which enables the selective isolation of this desired product (Villain, M.; Vizzavona, J.; Rose, K., Covalent capture: a new tool for the purification of synthetic and recombinant polypeptides. *Chemistry & Biology* 2001, 8 (7), 673-679; Toshiaki, H.; Akira, T.; Ken'ichiroh, N.; Takeshi, S.; Toru, K.; Saburo, A., Peptide purification by affinity chromatography based on α-ketoacyl group chemistry. *Journal of Peptide Science* 2009, 15 (5), 369-376; Toshiaki, H.; Akira, T.; Toru, K.; Saburo, A.; Michio, M., Peptide purification using the chemoselective reaction between N-(methoxy)glycine and isothiocyanato-functionalized resin. *Journal of Peptide Science* 2016, 22 (6), 379-382; Loibl, S. F.; Harpaz, Z.; Zitterbart, R.; Seitz, O., Total chemical synthesis of proteins without HPLC purification. *Chemical Science* 2016, 7 (11), 6753-6759).

Since for each coupling step a large excess of coupling reagent has to be added to the resin to ensure efficient capping, reagents, which are expensive or demand complex syntheses, are not useful for routine applications. The terminal modification of the full-length peptide, while avoiding high costs, raises another issue: either the final product after purification still contains the purification handle or parts thereof, or, if this is a problem for the e.g. bioactivity of the peptides, the use of traceless cleavable linkers is necessary. There are several traceless linkers described in the literature, but the cleavage conditions have to be carefully controlled to not contaminate the final product solution and to be innocuous for the peptide.

Reagents that facilitate the purification of compounds synthesized on a solid support are disclosed e.g. in WO 03/017930 A2.

A fluorous capping reagent for facile purification of peptides synthesized on the solid phase is disclosed e.g. in Montanari, V.; Kumar, K., Just add water: a new fluorous capping reagent for facile purification of peptides synthesized on the solid phase. *Journal of American Chemical Society* 2004, 126, 9528-9529.

Nitrogen-containing heterocyclic compounds comprising an activated carboxylic acid and a protected carbonyl group are disclosed e.g. in WO 2010/032437 A1.

The inventors were able to show that starting with comparatively cheap starting materials capping and capture reagents can be prepared. For efficient capping in solid phase peptide synthesis, often large excess of capping reagent has to be added in every synthesis cycle. Only a cheap and easily obtainable reagent is practical for routine use.

With the use of the inventive capping and capture reagents in solid phase peptide synthesis there is a significant time saving due to the possibility of parallelization of purifications compared to preparative HPLC purification. Furthermore, compared to conventional preparative HPLC, there is a solvent saving of up to about 200-fold. Terminated sequences which on HPLC co-elute with the desired product can be easily separated. With the use of a capping and capture reagent according to the present invention, no residual moieties are on the desired product compared to linker strategies with the capture of the full length peptide. Thus, there is also no need for final cleavage steps to obtain the final product (i.e. no contamination by cleavage or side products caused by harsh cleavage conditions).

Accordingly, in a first aspect, the present invention relates to the use of a capping and capture (cap-capt) reagent comprising a capping moiety and a capture moiety in solid phase peptide synthesis, wherein said capping moiety is a carboxylic acid or an activated carboxylic acid and wherein said capture moiety is a protected carbonyl group.

According to the present invention, the cap-capt reagent is used in solid phase peptide synthesis (SPPS). A solid phase peptide synthesis allows the rapid synthetic synthesis of a peptide chain by successive reactions of amino acid derivatives on a solid support. The solid support may consist of small, polymeric resin beads functionalized with reactive groups (such as amine or hydroxyl groups) that link to the emerging peptide chain. Each amino acid to be coupled to the peptide chain N-terminus must be protected on its N-terminus and side chain if it contains reactive functional groups like carboxy, hydroxyl or amino groups. Such protection may be achieved using appropriate protecting groups such as Boc (acid-labile) or Fmoc (fluorenylmethyloxycarbonyl) (base-labile) for the N-terminal amino group and orthogonal protecting groups for the side chains like tert-butyl, benzyl, tert-butyloxycarbonyl (Boc), 2,2,4,6,7-pentamethyldihydrobenzofurane-5-sulfonyl (Pbf), trityl, monomethoxytrityl (Mtr), benzyloxycarbonyl (Z), 1-(4,4-dimethyl-2,6-dioxocyclohex-1-ylidene)-3-methylbutyl (ivDde) or the like, depending on the side chain and the protection strategy used. The general SPPS procedure is a method of repeated cycles of alternate N-terminal deprotection and coupling reactions. The resin can be washed between each step. First a protected amino acid is coupled to the resin using a coupling or activation reagent like DIC/Oxyma or HBTU and a base like DIPEA. A capping step can optionally be applied thereafter to block unreacted amino groups from further reaction in the following coupling steps, using a capping reagent like acetic anhydride. Subsequently, the amine is deprotected, and then coupled with the free acid of the next amino acid. This cycle repeats until the desired sequence has been synthesized. At the end of the synthesis, the crude peptide is cleaved from the solid support while simultaneously removing all protecting groups using as reagent strong acids like trifluoroacetic acid (TFA) or a nucleophile. Scavengers may be added to TFA like water, thiols, sulfides or silanes. The crude peptide can be precipitated from a non-polar solvent like diethyl ether in order to remove organic soluble by-products.

During SPPS a full-length synthetic peptide of a desired sequence/composition can be obtained. However, despite the high efficiency of each coupling step, a small amount of amino acids on the growing peptide chain may not react with the successive amino acid, resulting in a shortened or failure peptide sequence. Failure peptide sequences represent the main by-products formed in SPPS. The fraction of failure peptide sequences compared to the main (full-length) synthetic peptide increases with increasing length and complexity of the peptide of choice. A failure peptide might be difficult or impossible to separate from the desired full-length synthetic peptide. A capping step as described herein—based on the capping and capture reagent described in the present disclosure—blocks the terminal amino groups of a failure peptide sequence, thereby preventing it from reacting in further coupling steps and from forming a peptide sequence with an amino acid deletion. Therefore, this cap-capt reagent also provides a means for purification of full-length synthetic peptides.

A "failure peptide" or "failure peptide sequence" according to the present disclosure is a peptide having an un-protected amino group on the penultimate amino acid after completion of an SPPS cycle. The person skilled in the art will understand that such shortened peptide is the result of an incomplete coupling reaction. In order to prevent a failure peptide from further coupling in a subsequent coupling step it might be capped, which is routinely done with acetic anhydride. Otherwise it might be activated and it might react in the next synthesis cycle and thereby lead to an "n-1"-peptide, i.e. a peptide that is very similar to the full-length synthetic peptide but shorter by one amino acid.

The capping and capture (cap-capt) reagent disclosed herein allows for capping a failure peptide sequence during peptide synthesis and for removal of the failure peptide sequence after solid phase peptide synthesis. The capping moiety reacts with a first reactive group located on the by-product of SPPS, such as the failure peptide, preventing the failure peptide sequence from further reacting. The capture moiety, which is part of the capping and capture reagent, allows for removal of those failure peptide sequences, by reacting the capture moiety chemoselectively with a further reactive group. Since the capture moiety is only present on a capped failure peptide sequence, but not on the full-length synthetic peptide any failure peptide can be easily separated from the desired full-length synthetic peptide.

A reactive group is a chemical group that is capable of forming a bond, preferably a covalent bond with another reactive group.

In the present case, the first reactive group is an amino group, especially the terminal amino group on a failure peptide. This terminal amino group reacts with the capping moiety of the cap-capt reagent disclosed herein.

The further or second reactive group is a reactive group which reacts with the capture moiety of the cap-capt reagent. The second reactive group is located on a solid support.

A suitable second reactive group is an amino oxy group or a hydrazine group.

According to the uses, methods and kits disclosed in the present invention, the cap-capt reagent comprises a capping moiety and a capture moiety, wherein the capping moiety is a carboxylic acid or an activated carboxylic acid.

The capture moiety according to the present invention is a protected carbonyl group. In one embodiment the protected carbonyl group is an acetal or a ketal.

A carboxylic acid is an organic compound that comprises a carboxyl group —C(O)OH.

In an embodiment of the present invention, the capping moiety of the cap-capt reagent is a carboxylic acid group.

The activation of the cap-capt reagent in its carboxylic acid form may be carried out by treatment with a coupling reagent. The activation may be performed prior to the addition of the cap-capt reagent to the failure peptide sequence. Alternatively, the activation of the cap-capt reagent may be carried out while already being in contact with the failure peptide sequence. In the latter case, the activation may be carried out with at least one of the reagents that are also used for the solid phase peptide synthesis. E.g. if a coupling reagent is used for the activation of the cap-capt reagent, the coupling reagent might be the same as the coupling reagent that is used for coupling the protected amino acid to build up the peptide sequence.

In one embodiment the capping moiety is an activated carboxylic acid. The person skilled in the art is familiar with the term activated carboxylic acid. An activated carboxylic acid is a carboxylic acid derivative highly susceptible towards nucleophilic attack. In one embodiment an activated carboxylic acid is a derivative of a carboxylic acid that is reactive with an amino group. In one example, an amino group on a failure peptide reacts with an activated carboxylic acid, resulting in the formation of an amide bond (or peptide bond).

Examples of activated carboxylic acids are acyl halides, anhydrides, pentafluorophenyl esters, N-hydroxysuccinimide esters or N-hydroxybenzotriazole esters or the like.

In an embodiment of the present invention, the cap-capture reagent comprises one capping moiety and one capture moiety.

In a further embodiment, the cap-capt reagent has Formula (I):

wherein

R1 is hydrogen or an optionally substituted alkyl,

R2 is OR5 or a halogen, each R3 and R4 is independently an optionally substituted alkyl, or form together with the oxygen atoms to which they are attached an optionally substituted 5-membered or 6-membered ring, R5 is selected from H, succinimide, pentafluorophenyl, benzotriazole, anhydride and and n is independently 0, 1, 2, 3 or 4.

An "alkyl" as used herein is a saturated branched or straight chemical group of the general formula $C_nH_{2n+1}$, preferably having 1 to 5 carbon atoms. An "optionally substituted alkyl" is a saturated branched or straight chemical group of the general formula $C_nH_{2n+1}$ in which at least one of the hydrogen atoms is replaced by a different group or atom, i.e. by a substituent. Examples of substituents are halogen, —CN, —NO$_2$, —C(O)N(R11)$_2$, —COO(R11), —O(R11), —N(R11)$_2$ with R11 being independently H or $C_1$-$C_3$ alkyl.

Optional substituents at the 5-membered or 6-membered ring which might be formed by each R3 and R4 with the oxygen atoms to which they are attached are e.g. alkyls like methyl or ethyl.

In one embodiment the activated carboxylic acid comprises an ester bond formed with a derivative of a suitable coupling reagent known in the art. Certain embodiments of the residue R2 or OR5, respectively, are those formed by reaction of carboxylic acids with carbodiimides like DCC (N,N'-dicyclohexylcarbodiimide), DIC (diisopropylcarbodiimide), EDC (1-ethyl-3-(3-dimethylaminopropyl)carbodiimide), EDAC (1-ethyl-3-(3-dimethylaminopropyl)carbodiimide) or WSC (water soluble carbodiimide) optionally in combination with additives such as HOBt (hydroxybenzotriazole), HOAt (1-Hydroxy-7-azabenzotriazole), HOOBt, (3-hydroxy-1,2,3-benzotriazin-4-one), HOSu, (N-hydroxysuccinimide), OxymaPure (2-cyano-2-(hydroxyimino)acetate) or DMAP (4-dimethylaminopyridine), phosphonium reagents such as BOP (benzotriazole-1-yl-oxy-tris-(dimethylamino)-phosphonium hexafluorophosphate), PyBOP (benzotriazol-1-yl-oxytripyrrolidinophosphonium hexafluorophosphate), PyBrOP, (3-hydroxy-1,2,3-benzotriazin-4-one), PyAOP ((7-Azabenzotriazol-1-yloxy)tripyrrolidinophosphonium hexafluorophosphate), PyOxim ([ethyl cyano(hydroxyimino)acetato-$O^2$]tri-1-pyrrolidinylphosphonium hexafluorophosphate), or DEPBT (3-(diethoxyphosphoryloxy)-1,2,3-benzotriazin-4(3H)-one), aminium/uraniumimonium reagents such as TBTU, HBTU ((2-(1H-benzotriazol-1-yl)-1,1,3,3-tetramethyluronium hexafluorophosphate), HCTU (O-(1H-6-Chlorobenzotriazole-1-yl)-1,1,3,3-tetramethyluronium hexafluorophosphate), HDMC (N-[(5-chloro-3-oxido-1H-benzotriazol-1-yl)-4-morpholinylmethylene]-N-methylmethanaminium hexafluorophosphate), TATU (O-(7-azabenzotriazole-1-yl)-N,N,N',N'-tetramethyluronium tetrafluoroborate), HATU (1-[Bis(dimethylamino)methylene]-1H-1,2,3-triazolo[4,5-b]pyridinium 3-oxid hexafluorophosphate), COMU ((1-cyano-2-ethoxy-2-oxoethylidenaminooxy)dimethylamino-morpholino-carbenium hexafluorophosphate), TOTT (2-(1-oxy-pyridin-2-yl)-1,1,3,3-tetramethylisothiouronium tetrafluoroborate), or TFFH (tetramethylfluoroformamidinium hexafluorophosphate), or other coupling reagents such as EEDQ (N-Ethoxycarbonyl-2-ethoxy-1,2-dihydroquinoline), T3P (propylphosphonic anhydride), DMTMM (4-(4,6-dimethoxy-1,3,5-triazin-2-yl)-4-methyl-morpholinium chloride), BTC (benzene-1,3,5-tricarboxylic acid) or CDI (1,1'-carbonyldiimidazole) (see e.g. Aldrich, ChemFiles, 2007, Vol. 7, No. 2, Peptide Synthesis).

In a further embodiment, the capping and capture reagent is selected from the group consisting of:

wherein

R6, R7, R8 and R9 are each independently selected from hydrogen and alkyl, and

R10 is optionally substituted alkyl.

In an embodiment, each of R6, R7, R8 and R9 are independently selected from hydrogen and $C_1$-$C_3$ alkyl.

Each of R6, R7, R8 and R9 may be hydrogen.

R10 may be methyl or ethyl.

R1 may be independently hydrogen, methyl or ethyl.

Residue R2, which is part of the capping moiety, may be independently selected from the group consisting of F, Cl and Br, O-succinimide, O-pentafluorophenyl, 0-benzotriazole, anhydride and

The cap-capt reagent may be selected from and

In a preferred embodiment, the cap-capt reagent is

A further aspect of the present invention relates to a method for solid phase peptide synthesis (SPPS) wherein individual amino acids are coupled to each other via Fmoc-chemistry, and, wherein after at least one coupling step a capping and capture reagent according to the present invention is used for capping a failure peptide sequence.

Fmoc represents 9-fluorenylmethyloxycarbonyl, a protecting group in organic chemistry synthesis.

In Fmoc chemistry, which represents a solid-phase peptide synthesis, the peptide chain is assembled stepwise, one amino acid at a time, while attached to an insoluble (resin) support. Amino acids are protected at their amino terminus by the Fmoc group and coupled to the growing chain after activation of their carboxylic acid terminus. The activated carboxylic acid of this amino acid reacts with the terminal amino group of the growing peptide chain. The Fmoc group is then removed by treatment with a base and the process repeated. After the peptide has been assembled it is removed from the insoluble resin support by treatment e.g. with trifluoroacetic acid (TFA). At the same time, protecting groups on amino acid side chains are also removed yielding the crude linear peptide.

In more detail a routine process for the synthesis of a peptide using stepwise solid-phase Fmoc-chemistry comprises the steps of: (a) swelling resin suited for peptide synthesis in a dipolar aprotic solvent, (b) if present, deprotecting the Fmoc group on the resin using a solution of piperidine in a dipolar aprotic solvent; (c) washing the resin after Fmoc deprotection with a dipolar aprotic solvent; (d) activating the Fmoc-amino acids for coupling to the deprotected resin by dissolving the Fmoc-amino acid, coupling reagent(s) (e.g. (2-(6-chloro-1H-benzotriazole-1-yl)-1,1,3, 3-tetramethylaminium hexafluorophosphate) (HCTU) or 2-(1H-benzotriazole-1-yl)-1,1,3,3-tetramethyluronium tetrafluoroborate (TBTU)/1-hydroxybenzotriazole (HOBt) with DIPEA) in a dipolar aprotic solvent; (e) charging the activated Fmoc-amino acid solution to the resin in the reactor; (f) coupling the activated Fmoc-amino acid to the N-terminal amino group on the resin; (g) washing the resin after each Fmoc-amino acid coupling; (h) optionally capping non-reacted amino groups, e.g. capping the failure peptide sequence, on the resin with a capping reagent (e.g. acetic anhydride); (i) repeating steps (b)-(h) until a full-length synthetic peptide is formed; (j) cleaving the desired peptide from the resin while simultaneously deprotecting the amino acid side chains using a cleavage cocktail; (j) filtering the cleavage mixture from the resin; and (k) evaporating the filtrates and/or precipitating and partially purifying the crude product from the concentrated solution with an organic solvent to yield a partially purified peptide.

As indicated in the general outline of a standard Fmoc synthesis above (cf. step (h), a capping step with acetic anhydride may be used to cap unreacted amino groups, especially the amino group on the unreacted penultimate amino acid of the desired peptide sequence. However, if acetic anhydride is used, it may be difficult to separate the full-length peptide from shortened peptides and usually sophisticated HPLC methods are required.

According to the uses and procedures disclosed herein, a failure peptide is capped with a capping and capture reagent according to the present disclosure in step (h) as outlined above. During said capping an amide bond between the capping moiety and an unprotected amino group (on the failure peptide sequence) is formed. This way at least one "failure peptide sequence" having reacted with the capping moiety of the cap-capt reagent and comprising the protected capture moiety and a full-length synthetic peptide, respectively, attached to the solid phase is obtained. In a SPPS method according to the present invention, a failure peptide sequence comprises, attached via the capping step, the cap-capt reagent.

In a further aspect, the present invention relates to a method for purification of (full-length) synthetic peptides comprising the steps of:
performing a solid phase peptide synthesis according to the present invention,
cleaving the compounds thus synthesized from the solid phase,
deprotecting the capture moiety, and
binding the deprotected capture moiety to a solid resin support, thereby binding the at least one failure peptide sequence to solid resin support and
separating the full-length synthetic peptide from the solid resin support comprising the failure peptide.

In a preferred embodiment, the solid resin support is an amino oxy resin, or a hydrazine resin.

The individual steps of a method for purification of (full-length) synthetic peptides are exemplified below.

After completion of the peptide synthesis, a synthetized peptide chain is cleaved off from the solid phase. This cleaving step is performed by the addition of appropriate reagents. Usually a strong acid like TFA (trifluoroacetic acid), TFA combined with scavengers (nucleophiles), e.g. a TFA mixture with additives such as water, silanes such as TES (triethylsilane) or TIS (triisopropylsilane), thiols such as mercaptoethanol, dithioerythritol (DTE), ethanedithiol (EDT) or dioxa-1,8-octane-dithiol (DODT), sulfides such as thioanisole or ethylmethylsulfide or ether such as anisole, is used.

While it may be possible to cleave off a synthesized full-length synthetic peptide from the solid phase without deprotection of protected capture moiety at the failure peptide, usually conditions will be chosen that accomplish both cleavage of a synthetic peptide from the solid support and deprotection of the capture moiety. Thereby, the capture moiety of the cap-capt reagent attached to the failure peptide (and the capture moiety of any cap-capt reagent still present) is deprotected. In a preferred embodiment, the deprotection step of the capture moiety is performed simultaneously to the cleavage step to cleave the peptides from the resin and to deprotect side chain amino acid protecting groups, thereby using the same reagent.

In an embodiment, the solid phase is filtrated from the mixture. In this embodiment, the filtrate preferably comprises a mixture of the full length synthetic peptide and a failure peptide comprising the cap-capt reagent attached to the failure peptide.

In an embodiment, the deprotected capture moiety of the cap-capt reagent bound to the failure peptide is bound to a resin comprising an amino group. In a preferred embodiment, the deprotected capture moiety is bound to an amino oxy resin, or to a hydrazine resin. The binding is accomplished by adding the respective amino oxy resin, or hydrazine resin to the deprotected capture moiety. With the binding step, a failure peptide sequence (capped via a cap-capt reagent) is bound to the amino oxy resin or hydrazine resin. The binding between the deprotected capture group and the amino oxy resin or hydrazine resin is generally achieved through an oxime or hydrazone bond.

The amino oxy resin as well as the hydrazine resin comprises a solid support. Solid supports are generally well known in the art and comprise beads, columns, arrays, multiwell plates, filters or other surface substrates. In one embodiment the amino oxy resin or the hydrazine resin, respectively is in form of a bead, column or filter. In one embodiment the amino oxy resin or the hydrazine resin, respectively is in form of a bead or a filter.

In a subsequent step, the full-length synthetic peptide is separated from the solid resin support, e.g. the amino oxy resin or the hydrazine resin, having bound thereto (via the cap-capt reagent) the failure peptide sequence. The separation can e.g. be accomplished by filtration, sedimentation, or centrifugation.

With the mentioned separation, an efficient and cost-effective purification of the synthesized synthetic peptides is possible. Such purification does not need a labor-intensive, costly and time-consuming HPLC-step. Rather several to many peptides synthesized according to the procedures disclosed herein can be purified economically and in parallel.

In a further aspect, the present invention is directed to a kit comprising a cap-capt reagent as described herein and at least one amino oxy resin or hydrazine resin.

In a further aspect, the present invention is directed to the use of a kit comprising a cap-capt reagent as described herein and at least one amino oxy resin or hydrazine resin for separation of full-length peptides from failure peptides sequences.

In a preferred embodiment, the kit is used for the purification of peptides obtained by solid phase peptide synthesis.

The use according to the invention may be further defined as specified for the method of the present invention. Particularly, with respect to the terms used in the further aspects of the present disclosure it is referred to the terms, examples and specific embodiments used in the first aspect of the present disclosure, which are also applicable to the further aspects of the present disclosure.

In general, the disclosure is not limited to the particular methodology, protocols, and reagents described herein because they may vary. Further, the terminology used herein is for the purpose of describing particular embodiments only and is not intended to limit the scope of the present disclosure. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the disclosure. Although any methods and materials similar or equivalent to those described herein can be used in the practice as presented herein, the specific methods, and materials are described herein.

The disclosure is further illustrated by the following figures and examples, although it will be understood that the figures and examples are included merely for purposes of illustration and are not intended to limit the scope of the disclosure unless otherwise specifically indicated.

FIGURES

FIG. 2 illustrates the capping and deprotection with reagents 1 and 2. A short peptide (WEGSKYA) was synthesized by standard Fmoc-based SPPS. After 5 couplings part of the resin was removed from the vessel, and treated with reagent 1 or reagent 2 (in DMF with a stoichiometric amount of lutidine). To deprotect and cleave these peptides from the resin a cleavage cocktail containing TFA, 5% anisole, 5% thioanisole and 5% water was used, because the use of triisopropylsilane has been described to cause reduction of aldehydes to alcohol. After 2 h treatment with the cleavage cocktail, the peptides were precipitated with cold diisopropyl ether and analysed by LCMS. This revealed that the capping with both reagents had occurred quantitatively, but while reagent 2 had been deprotected smoothly to yield the keto-capped peptide 5, reagent 1 was still quantitatively protected as acetal. The crude mixture was redissolved again in TFA and after 24 h at room temperature deprotection was finally observed.

FIG. 4a illustrates an HPLC chromatogram of a mixture of WEGSKYA (SEQ ID No. 1) 6 and keto-capped-GSKYA (SEQ ID No. 2) 5. FIG. 4b illustrates an HPLC chromatogram after 2 h incubation with amino-oxy resin 3.

FIG. 5a illustrates an HPLC chromatogram at 214 nm of a crude mixture of Angiotensin I and termination sequences after SPPS. FIG. 5b illustrates an HPLC chromatogram at 214 nm of Angiotensin I after incubation with amino-oxy resin 3. As model system the biological 10mer Angiotensin I (DRVYIHPFHL) (SEQ ID No. 3) was synthesized. To stress the conditions, single couplings with only one equivalent of amino acid per step were made. LCMS analysis of the crude material revealed a major termination after proline and further terminations after valine and tyrosine. All of them were quantitatively capped with reagent 2 (M+84) (FIG. 5a). The mixture was dissolved in acetate buffer at pH=4.5 and incubated on the amino oxy resin 3 for 2 h, obtaining full-length Angiotensin I (FIG. 5b) in good purity. Noteworthy is the complete removal of the keto-capped truncation Cap-PFHL (SEQ ID No. 4), which co-elutes with the main product.

FIG. 6 illustrates four HPLC chromatograms. As model peptide the 28mer des-octanoyl ghrelin (GSSFL-SPEHQRVQQRKESKKPPAKLQPR) (SEQ ID No. 5) was synthesized in a 20 μmol scale. After SPPS, crude des-octanoyl ghrelin was obtained with a purity of 72%. The crude product was dissolved in acetate buffer (pH=4.5, 0.1 M) and analyzed by HPLC-MS (FIG. 6a). The crude product was divided in two equal aliquots. The first was purified by preparative HPLC (FIG. 6b), the second was incubated for two hours on the amino-oxy resin 3 (FIG. 6c). The HPLC purification gave a purity of 99% and yield (respective to the initial resin loading) of 25%. The strategy with the cap-capt reagent gave a purity of 92% and yield of 48% (FIG. 6c). FIG. 6d illustrates the HPLC chromatogram when the product is subjected to a preparative HPLC.

EXAMPLES

Example 1

Figure 1:
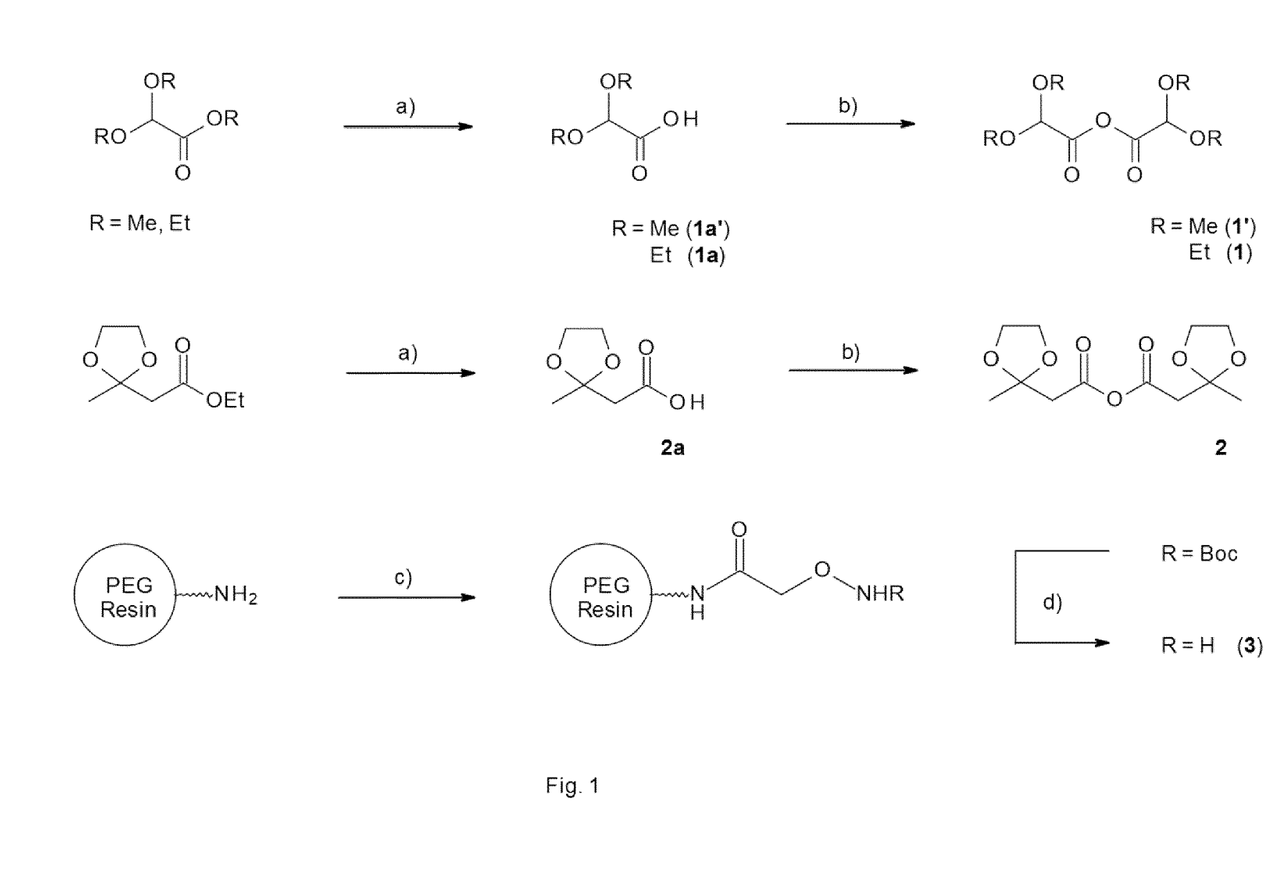
FIG. 1 illustrates the general reaction scheme for the synthesis of capping and capture reagents 1, or (1'), respectively, and 2 as well as of amino-oxy PEGA resin 3. Ethyl 2,2-diethoxyacetate and ethyl-2-methyl-1,3-dioxolane-2-acetate (fructone) were chosen as starting point for the synthesis of an aldehyde and a ketone containing capping moiety: the esters were hydrolyzed with NaOH (step a) and subsequently transformed to the corresponding symmetric anhydrides by treatment with dicyclohexylcarbodiimide (DCC) (step b).

General procedure for the ester hydrolysis (see also FIG. 1) (see Tartaggia, S.; Fogal, S.; Motterle, R.; Ferrari, C.; Pontini, M.; Aureli, R.; De Lucchi, O., Chemoenzymatic Synthesis of δ-Keto β-Hydroxy Esters as Useful Intermediates for Preparing Statins. *European Journal of Organic Chemistry* 2016, 2016 (19), 3162-3165): To a solution of methyl 2,2-dimethoxyacetate, ethyl 2,2-diethoxyacetate, or fructone (75 mmol) in EtOH (100 mL), respectively, was added NaOH (2 M aqueous solution, 50 mL). After stirring the reaction at r.t. for 4 h, EtOH was removed under reduced pressure. The aqueous phase was then washed with diisopropyl ether (2×20 mL), acidified with 2M HCl and extracted with EtOAc (3×100 mL). The combined organic fractions were dried over $Na_2SO_4$ and the solvent was removed under reduced pressure affording the desired product as slightly yellow oils (2,2-dimethoxyacetic acid (1a'); 2,2-diethoxyacetic acid (1a): 85%; 2a: 79%, respectively). I.e., compound 1 was obtained in a yield of 85% and compound 2 was obtained with a yield of 79%. This means that no chromatographic purification, but only an extraction in the first step and a filtration in the second step were necessary to obtain the capping reagents in good yield and purity. Scale up to up to 100 g anhydride in a single synthesis run was easily feasible. As basis for the capture resin a PEG based polymer (AminoPEGA® resin) was used, suitable for working with both organic and aqueous solvents. Boc-amino-oxy-acetic acid was installed on the resin (step c) and deprotected with TFA (step d) (see also FIG. 1).

The products were used for the next step without further purification.

General procedure for the anhydride synthesis (see also FIG. 1): To a solution of 2,2-dimethoxyacetic acid (1a'), 2,2-diethoxyacetic acid (1a) or 2-(2-methyl-1,3-dioxolan-2-yl)acetic acid (2a) (20 mmol) in $CH_2Cl_2$ at 0° C. was slowly added N, N-dicyclohexylcarbodiimide (10 mmol). The reaction was allowed to warm up to room temperature under vigorous stirring. After 3 h the reaction was filtrated, the solid removed and the solvent of the filtrate removed under reduced pressure affording the two anhydrides, respectively, in quantitative yield as slightly yellow resins, which were used without further purification.

2,2-dimethoxyacetic anhydride (1')

$^1$H NMR (400 MHz, CHLOROFORM-d) δ ppm 3.45 (s, 12H) 4.93 (s, 2H)

2,2-diethoxyacetic anhydride (1)

$^1$H NMR (400 MHz, CHLOROFORM-d) δ ppm 1.10 (t, 12H) 3.50 (q, 8H) 4.93 (s, 2H)

2-(2-methyl-1,3-dioxolan-2-yl)acetic anhydride (2)

$^1$H NMR (400 MHz, CHLOROFORM-d) δ ppm 1.50 (s, 6H) 2.82 (s, 4H) 3.98 (s, 8H)

Synthesis of the amino-oxy PEGA resin (3) (see also FIG. 1): Amino-PEGA-resin (Novabiochem, 1.00 g, loading 0.37 mmol/g) was washed with DMF (5×10 mL). Boc-amino-oxy-acetic acid (212 mg, 1.11 mmol), HATU (380 mg, 1.00 mmol) and DIPEA (383 μL, 2.2 mmol) were mixed in DMF (10 mL) and added to the resin. After 30 minutes shaking at room temperature the resin was washed with DMF, and a Kaiser test confirmed the absence of residual amino groups. Treatment of the resin with TFA+2% $H_2O$ for 1 h and subsequent washing with acetate buffer (0.1 M, pH=4.5) afforded the desired amino oxy resin.

Example 2

Peptide synthesis: Automated Fmoc based solid-phase peptide synthesis was performed by using a Syro I synthesizer and Rink-Amide Tentagel resin (loading 0.19 mmol/g). Fmoc deprotection was performed by treatment of the resin with 20% piperidine in DMF, 2×5 minutes. The successive Fmoc-protected amino acid (0.25 M in NMP+HOAt 0.25 M) was coupled on the resin using HCTU (0.8 M) and N-methyl morpholine (NMM, 3 M in DMF) for 15 min at room temperature. For each coupling, if not otherwise stated 5 equivalents amino acid (respectively to the resin loading) were used and the coupling repeated twice. Capping of residual free amino functions was performed by treatment of the resin with 2-(2-methyl-1,3-dioxolan-2-yl)acetic anhydride (2) and lutidine (both 0.5 M in DMF; 20 equivalents, respectively, to the resin loading). Cleavage from the resin was performed using TFA/thioanisole/anisole/$H_2O$ (85:5:5:5). The resin was incubated for 30 minutes with this cocktail and then the cleavage solution was kept for 1-2 hours at room temperature. After reduction of the volume of the solution under nitrogen stream, crude peptides were obtained by precipitation with diisopropyl ether and centrifugation.

Example 3

Figure 3:
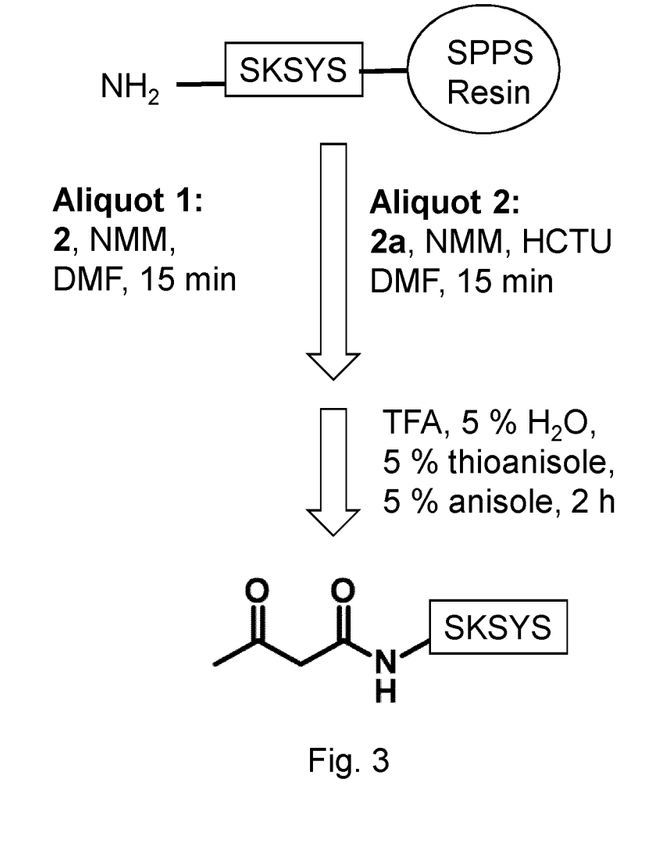
FIG. 3 illustrates the capping of the peptide sequence with a cap-capt reagent according to the present invention.

The peptide sequence H—SKSYS-Resin (SEQ ID No. 6) (10 μmol) was synthesized according to the standard method described above (but using acetic anhydride instead of 2 for capping). The resin was divided in 2 equal parts (each 5 µmol). The first aliquot was treated with a solution of 2 (0.5 M in DMF, 0.5 mL) and NMM (N-methylmorpholine) (3 M in DMF, 100 µL) for 15 minutes. The second aliquot (Aliquot 2) was treated with a solution of 2a (0.5 M in DMF, 0.5 mL), NMM (3 M in DMF, 100 µL) and HCTU (2-(6-Chlor-1H-benzotriazol-1-yl)-1,1,3,3-tetramethylaminium-hexafluorophosphat) (0.8 M in DMF, 250 µL) for 15 minutes. Cleavage from the resin was performed using TFA/thioanisole/anisole/H$_2$O (85:5:5:5). Both capping methods showed full capping of the terminal amino group. (FIG. 3).

MS (ESI): 654.28 [M+H]$^+$

Example 4

Figure 2:
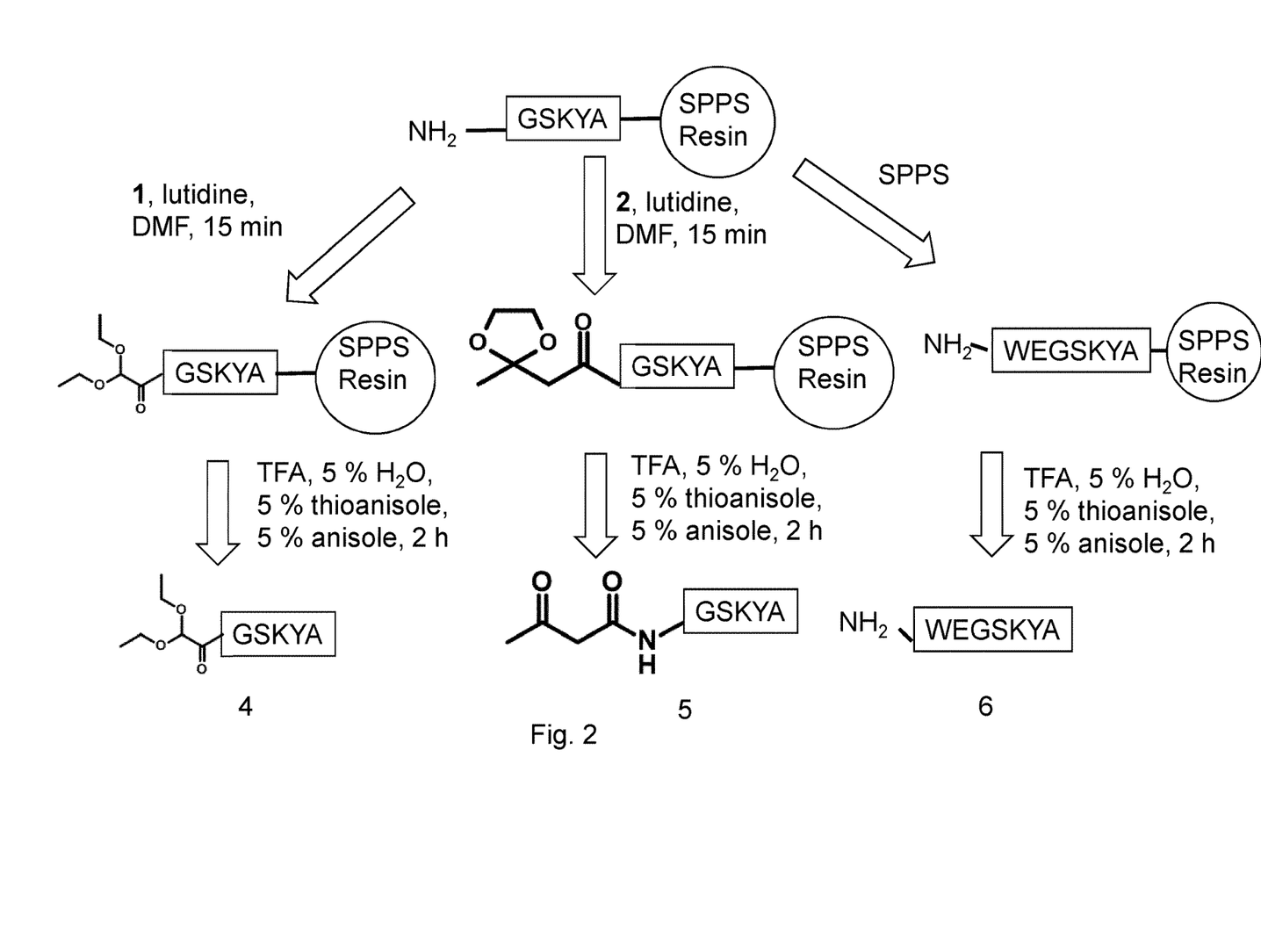

The peptide sequence H-GSKYA-Resin (SEQ ID No. 7) (15 µmol) was synthesized according to the standard method described above (but using acetic anhydride instead of 2 for capping). As illustrated in FIG. 2, the resin was divided in 3 equal parts (each 5 µmol). The first aliquot (Aliquot 1) was treated with a solution of 1 (50 µmol) and 2,6-lutidine (50 µmol) in DMF (1 mL) for 15 minutes. The second aliquot (Aliquot 2) was treated with a solution of 2 (50 µmol) and 2,6-lutidine (50 µmol) in DMF (1 mL) for 15 minutes. Cleavage from the resin was performed using TFA/thioanisole/anisole/H$_2$O (85:5:5:5). Both Aliquot 1 and Aliquot 2 showed full capping of the terminal amino group. While the acetal of Aliquot 2 was completely deprotected generating the corresponding ketone, the acetal protection of Aliquot 1 was still intact after the cleavage procedure. The remaining aliquot (Aliquot 3) was subjected to two further solid phase synthesis steps, with following cleavage from the resin, generating peptide H-WEGSKYA.

Example 5

Figure 4:
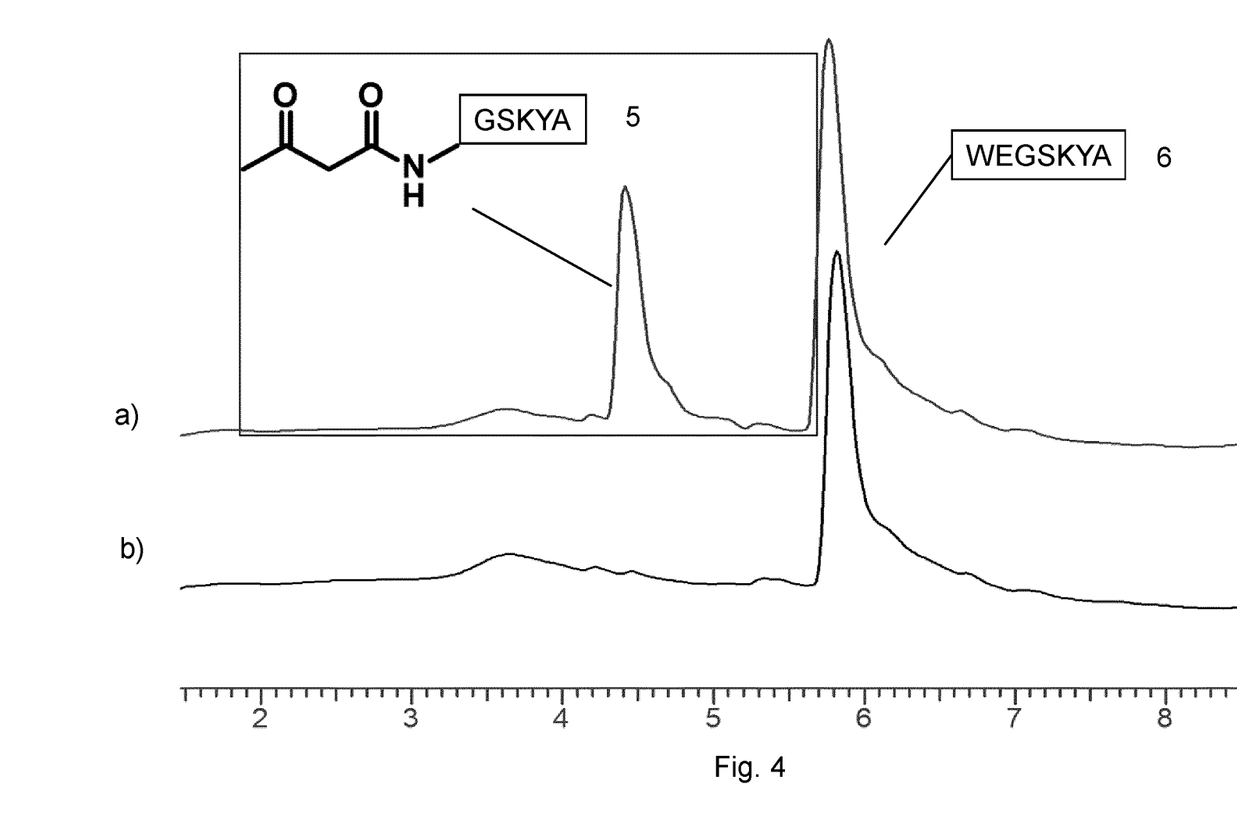
FIG. 4 illustrates two HPLC chromatograms.

Keto capped GSKYA (SEQ ID No. 2) (5) (1 µmol) and H-WEGSKYA (SEQ ID No. 1) (6) (1 µmol) were dissolved in acetate buffer (0.1 M, pH=4.5) and analyzed by HPLC-MS (FIG. 4a). Amino-oxy PEGA resin (3) was added to the mixture and after 2 h the supernatant was analysed by HPLC-MS, showing only 6 left in solution (FIG. 4b).

Example 6

Figure 5:
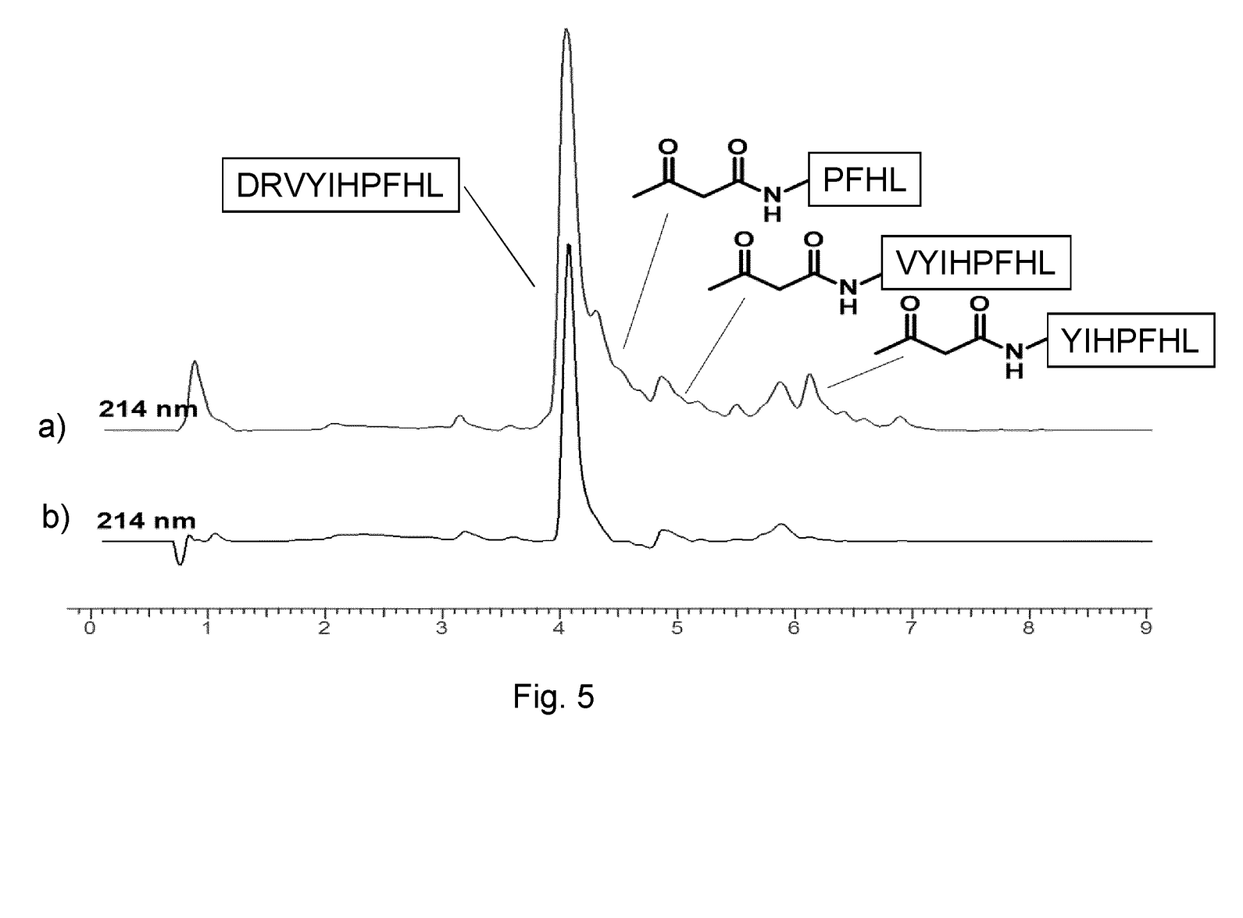
FIG. 5 illustrates two HPLC chromatograms.

Angiotensin I was synthesized according to the procedure described above with a modification in the amount of amino acid used for the couplings: instead of 2×5 equivalents Fmoc-amino acid, a single coupling with 1 equivalent amino acid was performed. The crude product was dissolved in acetate buffer (0.1 M, pH=4.5) and analyzed by HPLC-MS (Figure 5a). Amino-oxy PEGA resin (3) was added to the mixture and after 2 h the supernatant was analysed by HPLC-MS, showing the successful removal of most impurities (FIG. 5 b).

Example 7

Figure 6:
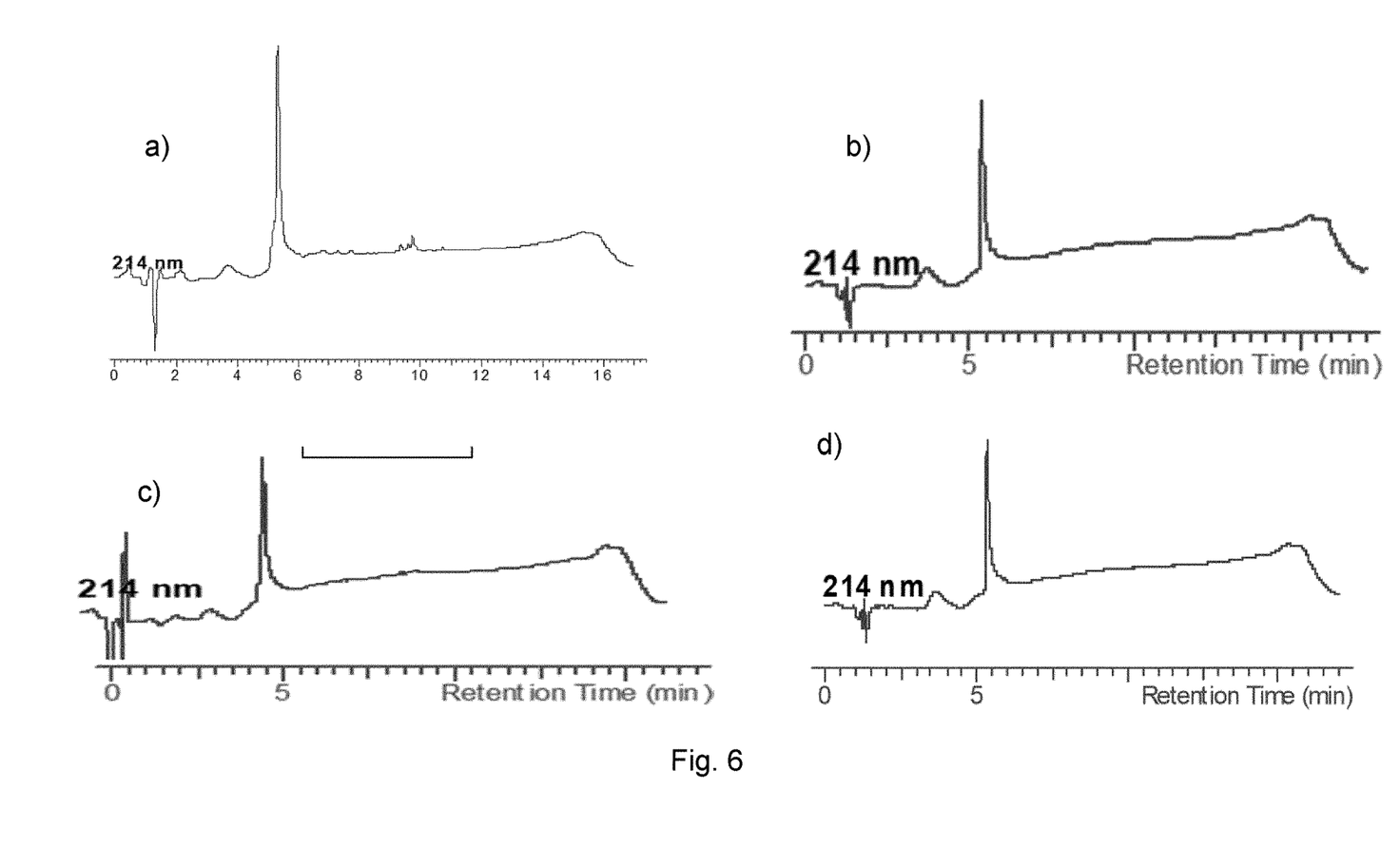
Figure 7:
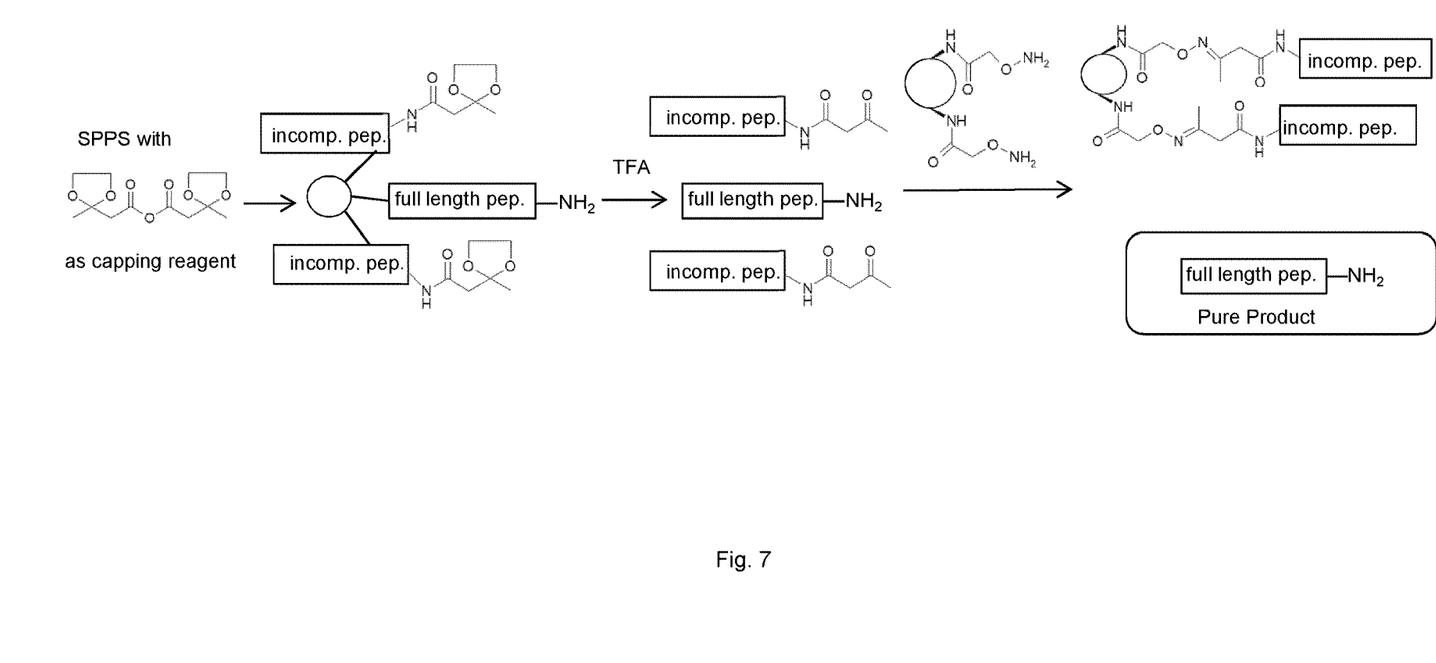
FIG. 7 is a schematic illustration of the use of a capping and capture reagent for HPLC free purification of peptides. During the acidic cleavage and deprotection of the peptides the acetal containing capping moiety is transformed into a ketone, which can be chemoselectively captured by an amino-oxy resin. The full length peptide remains in solution as pure product.

Des-octanoyl ghrelin (GSSFLSPEHQRVQQRKESKKP-PAKLQPR) (SEQ ID No. 5) (20 µmol) was synthesized according to the general peptide synthesis procedure described above. The crude product was dissolved in acetate buffer (0.1 M, pH=4.5) and analyzed by HPLC-MS (FIG. 6a), and resulted to contain 72% of the desired product. The mixture was divided in 2 aliquots. The first was purified by preparative HPLC, affording the desired product in 99% purity and 25% yield (FIG. 6b). The second aliquot was incubated for 2 h with the Amino-oxy PEGA resin (3). The desired product was isolated in 92% purity and 48% yield (FIG. 6c). Subjecting this product to a preparative HPLC chromatography the product could be isolated with a final purity of 99% and overall 30% yield (FIG. 6d).

|  | HPLC purification | purification with a capcapt reagent according to the present invention |
|---|---|---|
| purity | 99% | 92% |
| yield | 25% | 48% |
| solvent | 1200 mL | 10 mL |
| parallel purifications | not possible | possible |

---

The invention claimed is:

1. A method for purification of a synthetic peptide comprising the steps of:

performing a solid phase peptide synthesis (SPPS), wherein individual amino acids are coupled to each other via Fmoc-chemistry, wherein after at least one coupling step a capping and capture reagent is used for capping a failure peptide sequence, said capping and capture (cap-capt) reagent comprising a capping moiety and a capture moiety, and wherein said capping moiety is a carboxylic acid or an activated carboxylic acid and wherein said capture moiety is a protected carbonyl group, the capping and capture reagent being selected from and cleaving the compounds thus synthesized from the solid phase by adding trifluoroacetic acid (TFA) or TFA combined with one or more scavengers, wherein said one or more scavengers are selected from water, a silane, a thiol, a sulfide, and/or an ether, deprotecting the capture moiety using trifluoroacetic acid (TFA) or TFA combined with one or more scavengers, wherein said one or more scavengers are selected from water, a silane, a thiol, a sulfide, and/or an ether, and binding the deprotected capture moiety to a solid resin support thereby binding the at least one failure peptide sequence to the solid resin support and separating the synthetic peptide from the solid resin support comprising the failure peptide.

2. Method according to claim 1, wherein the solid resin support is an amino oxy resin, or hydrazine resin.

3. Method according to claim 1, wherein the separating of the peptide from the solid resin support comprising the failure peptide is carried out by centrifugation or by filtration.

4. The method according to claim 1, wherein the one or more scavengers is selected from triethylsilane, triisopropylsilane, mercaptoethanol, dithioerythritol, ethanedithiol, dioxa-1,8-octane-dithiol, thioanisole, ethylmethylsulfide, and/or anisole.

* * * * *